US007196057B2

(12) United States Patent
Gatehouse et al.

(10) Patent No.: US 7,196,057 B2
(45) Date of Patent: Mar. 27, 2007

(54) FUSION PROTEINS FOR INSECT CONTROL

(75) Inventors: John Arthur Gatehouse, Durham (GB); Elaine Charlotte Fitches, York (GB); John Patrick Edwards, York (GB)

(73) Assignees: University of Durham, Durham (GB); Department for Enviroment, Food And Rural Affairs, London (GB)

( * ) Notice: Subject to any disclaimer, the term of this patent is extended or adjusted under 35 U.S.C. 154(b) by 176 days.

(21) Appl. No.: 10/486,234

(22) PCT Filed: Jun. 8, 2002

(86) PCT No.: PCT/GB02/03598

§ 371 (c)(1),
(2), (4) Date: Feb. 9, 2004

(87) PCT Pub. No.: WO03/014150

PCT Pub. Date: Feb. 20, 2003

(65) Prior Publication Data

US 2005/0054821 A1 Mar. 10, 2005

(30) Foreign Application Priority Data

Aug. 8, 2001 (GB) .................. 0119274.9

(51) Int. Cl.
*C07K 14/00* (2006.01)
(52) U.S. Cl. .......................... 514/2; 530/350
(58) Field of Classification Search ................ 530/350; 514/2
See application file for complete search history.

(56) References Cited

U.S. PATENT DOCUMENTS

| 5,023,171 | A | | 6/1991 | Ho et al. |
| 5,284,760 | A | | 2/1994 | Feinstone et al. |
| 5,286,632 | A | | 2/1994 | Jones |
| 5,545,820 | A | * | 8/1996 | Gatehouse et al. .......... 800/279 |
| 5,556,747 | A | | 9/1996 | Kumar |
| 5,580,759 | A | | 12/1996 | Yang et al. |
| 5,686,600 | A | * | 11/1997 | Carozzi et al. .......... 536/23.53 |
| 5,843,660 | A | | 12/1998 | Schumm et al. |
| 6,358,679 | B1 | | 3/2002 | Heid et al. |

OTHER PUBLICATIONS

Lerner et al. 1992; The Gene for Stinging Nettle Lectin (*Urtica dioica* Agglutin) Encodes Both a Lectin and a Chitinase. J. Biol. Chem. 267(16): 11085-11091.*
Svinth et al. 1998; Differences in Cytotoxicity of Native and Engineered RIPs Can Be Used to Assess Their Ability to Reach the Cytoplasm. Biochem. Biophys. Rex. Commun. 249:637-642.*
Beaumelle et al. 1997; Ricin A Chain Can Transport Unfolded Dihydrofolate Reductase into the Cytosol. J. Biol. Chem 272(35):22097-22102.*
Fitches et al. 2001; The Effects of *Phaseolus vulgaris* Erythro- and Leucoagglutinating Isolectins (PHA-E and PHA-L) Delivered Via Artificial Diet and Transgenic Plants on the Growth and Development of Tomato Moth (*Laconobia oleracea*) Larvae: Lectin Binding to Gut Glycoproteins In Vitro and In Vivo J. Insect Physiology 47: 1389-1398.*
Fitches et al. 2002; Fusion Proteins Containing Neuropeptides as Novel Insect Control Agents: Snowdrop Lectin Delivers Fused Allatostatin to Insect Haemolymph Following Oral Ingestion. Insect Biochemistry and Molecular Biology 32: 1653-1661.*
Fitches et al. 2004; Fusion Proteins Containing Insect-Specific Toxins as Pest Control Agents : Snowdrop Lectin Delivers Fused Insecticidal Spider Venom Toxin to Insect Haemolymph Following Oral Ingestion. J. Insect Physiology. 50: 61-71.*
Fitches et al. 2004; Cloning, Expression and Functional Characterisation of Chitinase from Larvae of Tomato Moth (*Laconobia oleracea*): A Demonstration of the Insecticidal Activity of Insect Chitinase. Insect Biochemistry and Molecular Biology 34: 1037-1050.*
Gade et al. 2003; Insect Peptide Hormones: A Selective Review of Their Physiology and Potential Application for Pest Control. Pest Management Science 59:1063-1075.*
RM Horton, HD Hunt, SN Ho, JK Pullen, LR Pease—Engineering Hybrid Genes Without the Use of Restriction Enzymes; Gene Splicing by Overlap Extension Gene. Apr. 15, 1989;77(1):61-8.
W Ito, H Ishiguro, Y Kurosawa—A General Method for Introducing a Series of Mutations into Cloned DNA Using the Polymerase Chain Reaction Gene. Jun. 15, 1991;102(1):67-70.
RM Horton, ZL Cai, SN Ho, LR Pease—Gene Splicing by Overlap Extension: Tailor-Made Genes Using the Polymerase Chain Reaction Gene. Jun. 15, 1991;102(1):67-70.
SN Ho, HD Hunt, RM Horton, JK Pullen, LR Pease—Site-Directed Mutagenesis by Overlap Extension Using the Polymerase Chain Reaction Gene. Apr. 15, 1989;77(1):51-9.
BN Beck, SN Ho—Increased Specificity of PCR-Amplified Products by Size-Fractionation of Restriction Enzyme-Digested Template Genomic DNA Nucleic Acids Res. Sep. 26, 1988;16(18):9051.
M Rodriguez, AK Patrick, LR Pease, CS David—Role of T Cell Receptor V Beta Genes in Theiler's Virus-Induced Demyelination of Mice J Immunol. Feb. 1, 1992;148(3):921-7.

(Continued)

*Primary Examiner*—Karen Cochrane Carlson
(74) *Attorney, Agent, or Firm*—Jacobson Holman PLLC

(57) ABSTRACT

A fusion protein comprising a translocating moiety and a toxic moiety wherein the translocating moiety comprises a plant protein that is capable of acting as a carrier to translocate the toxic moiety across the gut wall of at least one plant pathogen, wherein the toxic moiety is adapted to be effective as a toxic agent following translocation; composition comprising the protein, methods for preparation thereof; polynucleotide encoding the fusion protein, vector comprising the polynucleotide, host cell and transgenic plant cell or plant that is resistant to pathogen, expressing the fusion protein, and uses thereof in combatting plant pathogens and in insect control.

24 Claims, 6 Drawing Sheets

OTHER PUBLICATIONS

Figure 1:
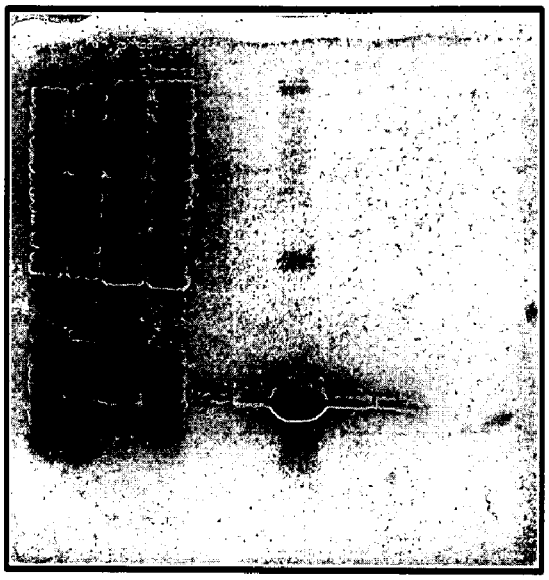
Figure 1:

H Kadowaki, T. Kadowaki, FE Wondisford, SI Taylor—Use of Polymerase Chain Reaction Catalyzed by Taq DNA Polymerase for Site-Specific Mutagenesis Gene. Mar. 15, 1989;76(1):161-6.

XJ Yang, CQ Chen, DB Wang, SL Yang—An Efficient Site-Directed Mutagenesis Using Polymerase Chain Reaction Sci China B. Jun. 1991;34(6):712-8.

Q Liang, L Chen, AJ Fulco—An Efficient and Optimized PCR Method with High Fidelity for Site-Directed Mutagenesis PCR Methods Appl. Apr. 1995;4(5):269-74.

YA Berlin—DNA Splicing by Directed Ligation (SDL) Curr Issues Mol Biol. 1999;1(1-2):21-30.

RM Horton, SN Ho, JK Pullen, HD Hunt, Z Cai, LR Pease—Gene Splicing by Overlap Extension Methods Enzymol. 1993;217:270-9.

F Vallette, E Mege, A Reiss, M Adesnik—Construction of Mutant and Chimeric Genes Using the Polymerase Chain Reaction Nucleic Acids Res. Jan. 25, 1989;17(2):723-33.

RM Nelson, GL Long—A General Method of Site-Specific Mutagenesis Using a Modification of the Thermus Aquaticus Polymerase Chain Reaction Anal Biochem. Jul. 1989;180(1):147-51.

DH Jones, BH Howard—A Rapid Method for Recombination and Site-Specific Mutagenesis by Placing Homologous Ends on DNA Using Polymerase Chain Reaction Biotechniques. Jan. 1991;10(1):62-6.

O Landt, HP Grunert, U Hahn—A General Method for Rapid Site-Directed Mutagenesis Using the Polymerase Chain Reaction Gene. Nov. 30, 1990;96(1):125-8.

RM Horton—PCR-Mediated Recombination and Mutagenesis. SOEing Together Tailor-Made Genes Mol Biotechnol. Apr. 1995;3(2):93-9.

DH Jones, SC Winistorfer—Recombinant Circle PCR and Recombination PCR for Site-Specific Mutagenesis Without PCR Product Purification Biotechniques. Apr. 1992;12(4):528-30, 532, 534-5.

HG Morrison, RC Desrosiers—A PCR-Based Strategy for Extensive Mutagenesis of a Target DNA Sequence Biotechniques, Mar. 1993;14(3):454-7.

GJ Chang, BJ Johnson, DW Trent—Site-Specific Oligonucleotide-Directed Mutagenesis Using T4 DNA Polymerase DNA PMID: 3286164 [PubMed—indexed for MEDLINE] Apr. 1988;7(3):211-7.

A Urban, S Neukirchen, KE Jaeger—A Rapid and Efficient Method for Site-Directed Mutagenesis Using One-Step Overlap Extension PCR Nucleic Acids Res. Jun. 1, 1997;25(11):2227-8.

RD Kirsch, E Joly—An Improved PCR-Mutagenesis Strategy for Two-Site Mutagenesis or Sequence Swapping Between Related Genes Nucleic Acids Res. Apr. 1, 1998;26(7):1848-50.

Q Mo, X Xu, X Zhong, Z Liu—An Improved PCR-Based Megaprimer Method for Site-Directed Mutagenesis Zhonghua Yi Xue Yi Chuan Xue Za Zhi. Feb. 2002;19(1):68-71.

S Herlitze, M Koenen—A General and Rapid Mutagenesis Method Using Polymerase Chain Reaction Gene. Jul. 2, 1990;91(1):143-7.

K Majumder—Ligation-Free Gene Synthesis by PCR: Synthesis and Mutagenesis at Multiple Loci of a Chimeric Gene Encoding OmpA Signal Peptide and Hirudin Gene. Jan. 2, 1992;110(1):89-94.

L Young, Q Dong—TAMS Technology for Simple and Efficient in Vitro Site-Directed Mutagenesis and Mutant Screening Nucleic Acids Res. Feb. 1, 2003;31(3):e11.

MM Ling, BH Robinson—Approaches to DNA Mutagenesis: An Overview Anal Biochem. Dec. 15, 1997;254(2):157-78.

F Allemandou, J Nussberger, HR Brunner, N Brakch—Rapid Site-Directed Mutagenesis Using Two-PCR-Generated DNA Fragments Reproducing the Plasmid Template J Biomed Biotechnol. 2003;2003(3):202-207.

A Seyfang, JH Jin—Multiple Site-Directed Mutagenesis of More than 10 Sites Simultaneously and in a Single Round Anal Biochem. Jan. 15, 2004;324(2):285-91.

AN Vallejo, RJ Pogulis, LR Pease—In Vitro Synthesis of Novel Genes: Mutagenesis and Recombination by PCR PCR Methods Appl. Dec. 1994;4(3):S123-30.

GJ Rouwendal, EJ Wolbert, LH Zwiers, J Springer—Simultaneous Mutagenesis of Multiple Sites: Application of the Ligase Chain Reaction Using PCR Products Instead of Oligonucleotides Biotechniques. Jul. 1993;15(1):68-70, 72-4, 76.

S Byrappa, DK Gavin, KC Gupta—A Highly Efficient Procedure for Site-Specific Mutagenesis of Full-Length Plasmids Using Vent DNA Polymerase Genome Res. Nov. 1995;5(4):404-7.

SD Senanayake, DA Brian—Precise Large Deletions by the PCR-Based Overlap Extension Method Mol Biotechnol. Aug. 1995;4(1):13-5.

W Wang, BA Malcolm—Two-Stage Polymerase Chain Reaction Protocol Allowing Introduction of Multiple Mutations, Deletions, and Insertions, Using QuikChange Site-Directed Mutagenesis Methods Mol Biol. 2002;182:37-43.

SL Berger, RE Manrow, HY Lee—Phoenix Mutagenesis: One-Step Reassembly of Multiply Cleaved Plasmids with Mixtures of Mutant and Wild-Type Fragments Anal Biochem. Nov. 1, 1993;214(2):571-9.

SH Ke, EL Madison—Rapid and Efficient Site-Directed Mutagenesis by Single-Tube 'Megaprimer' PCR Method Nucleic Acids Res. Aug. 15, 1997;25(16):3371-2.

RJ Pogulis, AN Vallejo, LR Pease—In Vitro Recombination and Mutagenesis by Overlap Extension PCR Methods Mol Biol. 1996;57:167-76.

A Aiyar, Y Xiang, J Leis—Site-Directed Mutagenesis Using Overlap Extension PCR. Methods Mol Biol. 1996;57:177-91.

I Rabhi, N Guedel, I Chouk, K Zerria, MR Barbouche, K Dellagi, DM Fathallah—A Novel Simple and Rapid PCR-Based Site-Directed Mutagentis Method. Mol Biotechnol. Jan. 2004;26(1):27-34.

NA Shevchuk, AV Bryksin, YA Nusinovich, FC Cabello, M Sutherland, S Ladisch—Construction of Long DNA Molecules Using Long PCR-Based Fusion of Several Fragments Simultaneously Nucleic Acids Res. Jan. 22, 2004:32(2):e19.

GJ Chang, BJ Johnson, DW Trent—Site-Specific Oligonucleotide-Directed Mutagenesis Using T4 DNA Polymerase DNA, Apr. 1988;7(3):211-7.

A Urban, S Neukirchen, KE Jaeger—A Rapid and Efficient Method for Site-Directed Mutagenesis Using One-Step Overlap Extension PCR Nucleic Acids Res. Jun. 1, 1997;25(11):2227-8.

KE Song-Hua, EL Madison—Rapid and Efficient Site Directed Mutagenesis by Single-Tube 'Megaprimer' PCR Method Oxford University Press 1995:3371-3372.

* cited by examiner

(A) (B)

(A)

1 2 34  5 6 78 910

(B)

1 2 3 4

(A)

(B)

Table 1. Amino acid composition analysis of Mas-AS

| Amino acid | Native | | RCM | |
|---|---|---|---|---|
| | Found | Best integral value | Found | Best integral value |
| Asx | 1.4 | 1 | 1.1 | 1 |
| Glx | 3.0 | 3 | 2.1 | 2 |
| Ser | 2.1 | 2 | 0.9 | 1 |
| His | 0.4 | 0 | 0.1 | 0 |
| Gly | 2.0 | 2 | 0.4 | 0 |
| Thr | 0.7 | 1 | 0.3 | 0 |
| Ala | 0.9 | 1 | 0.4 | 0 |
| Arg | 2.2 | 2 | 1.9 | 2 |
| Tyr | 1.2 | 1 | 1.0 | 1 |
| Val | 1.0 | 1 | 0.9 | 1 |
| Met | 0.3 | 0 | 0.1 | 0 |
| Ile | 1.1 | 1 | 1.0 | 1 |
| Phe | 2.5 | 3 | 2.7 | 3 |
| Leu | 0.5 | 1 ? | 0.2 | 0 |
| Lys | 0.5 | 1 ? | 0.3 | 0 |
| Pro | 1.1 | 1 | 0.8 | 1 |
| Cys | | 2 | 1.7 | 2 |

Figure 6

SEQUENCE LISTING

<160> NUMBER OF SEQ ID NOS: 17

<210> SEQ ID NO 1
<211> LENGTH: 402
<212> TYPE: DNA
<213> ORGANISM: Artificial
<220> FEATURE:
<223> OTHER INFORMATION: Fusion protein  GNA/Manse-AS includes
      restriction sites introduced by PCR for cloning into pET14b.
      Fragments include GNA, linker and Manse-AS.

<400> SEQUENCE: 1

```
catatggaca atattttgta ctccggtgag actctctcta caggggaatt tctcaactac      60
ggaagtttcg tttttatcat gcaagaggac tgcaatctgg tcttgtacga cgtggacaag     120
ccaatctggg caacaaacac aggtggtctc tcccgtagct gcttcctcag catgcagact     180
gatgggaacc tcgtggtgta caacccatcg aacaaaccga tttgggcaag caacactgga     240
ggccaaaatg ggaattacgt gtgcatccta cagaaggata ggaatgttgt gatctacgga     300
actgatcgtt gggctactgg aactcacacc ggatccgggg gcatatgca ggtgcgcttc      360 cgccagtgct acttcaaccc catctcctgc ttctgaggat cc                        402
```

<210> SEQ ID NO 2
<211> LENGTH: 342
<212> TYPE: DNA
<213> ORGANISM: Snow drop lectin

<400> SEQUENCE: 2

```
catatggaca atattttgta ctccggtgag actctctcta caggggaatt tctcaactac      60
ggaagtttcg tttttatcat gcaagaggac tgcaatctgg tcttgtacga cgtggacaag     120
ccaatctggg caacaaacac aggtggtctc tcccgtagct gcttcctcag catgcagact     180
gatgggaacc tcgtggtgta caacccatcg aacaaaccga tttgggcaag caacactgga     240
ggccaaaatg ggaattacgt gtgcatccta cagaaggata ggaatgttgt gatctacgga     300
actgatcgtt gggctactgg aactcacacc ggatgaggat cc                        342
```

<210> SEQ ID NO 3
<211> LENGTH: 16
<212> TYPE: PRT
<213> ORGANISM: C. Vomitoria

<400> SEQUENCE: 3

```
Asp Pro Leu Asn Glu Glu Arg Arg Ala Asn Arg Tyr Gly Phe Gly Leu
1               5                   10                  15
```

```
<210> SEQ ID NO 4
<211> LENGTH: 14
<212> TYPE: PRT
<213> ORGANISM: C. Vomitoria

<400> SEQUENCE: 4

Leu Asn Glu Glu Arg Arg Ala Asn Arg Tyr Gly Phe Gly Leu
1               5                   10

<210> SEQ ID NO 5
<211> LENGTH: 8
<212> TYPE: PRT
<213> ORGANISM: C. Vomitoria

<400> SEQUENCE: 5

Ala Asn Arg Tyr Gly Phe Gly Leu
1               5

<210> SEQ ID NO 6
<211> LENGTH: 8
<212> TYPE: PRT
<213> ORGANISM: C. Vomitoria

<400> SEQUENCE: 6

Asp Arg Pro Tyr Ser Phe Gly Leu
1               5

<210> SEQ ID NO 7
<211> LENGTH: 8
<212> TYPE: PRT
<213> ORGANISM: C. Vomitoria

<400> SEQUENCE: 7

Asn Arg Pro Tyr Ser Phe Gly Leu
1               5

<210> SEQ ID NO 8
<211> LENGTH: 8
<212> TYPE: PRT
<213> ORGANISM: C. Vomitoria

<400> SEQUENCE: 8

Gly Pro Pro Tyr Asp Phe Gly Met
1               5

<210> SEQ ID NO 9
<211> LENGTH: 28
<212> TYPE: DNA
<213> ORGANISM: Artificial
<220> FEATURE:
<223> OTHER INFORMATION: 5' GNA/Nde I Oligonucleotide primer

<400> SEQUENCE: 9
taatcatatg gacaatattt tgtactcc                                           28

<210> SEQ ID NO 10
<211> LENGTH: 30
<212> TYPE: DNA
<213> ORGANISM: Artificial
<220> FEATURE:
<223> OTHER INFORMATION: 3' GNA/BAC109 Oligonucleotide primer

<400> SEQUENCE: 10
attaggatcc tcatccggtg tgagttccag                                         30
```

-continued

<210> SEQ ID NO 11
<211> LENGTH: 24
<212> TYPE: DNA
<213> ORGANISM: Artificial
<220> FEATURE:
<223> OTHER INFORMATION: 3' GNA/Bam HI Oligonucleotide primer

<400> SEQUENCE: 11
taatggatcc ggtgtgagtt ccag                                          24

<210> SEQ ID NO 12
<211> LENGTH: 65
<212> TYPE: DNA
<213> ORGANISM: Artificial
<220> FEATURE:
<223> OTHER INFORMATION: 5' Manse-AS Oligonucleotide primer

<400> SEQUENCE: 12
gatccggggg gcatatgcag gtgcgcttcc gccagtgcta cttaaccccca tctcctgctt   60 ctgag                                                               65

<210> SEQ ID NO 13
<211> LENGTH: 66
<212> TYPE: DNA
<213> ORGANISM: Artificial
<220> FEATURE:
<223> OTHER INFORMATION: 3' Manse-AS Oligonucleotide primer

<400> SEQUENCE: 13
gatcctcaga agcaggagat ggggttaaag tagcactggc ggaagcgcac ctgcatatgc    60
cccccg                                                              66

<210> SEQ ID NO 14
<211> LENGTH: 13
<212> TYPE: PRT
<213> ORGANISM: Artificial
<220> FEATURE:
<223> OTHER INFORMATION: Fusion protein of P. Americana Allostatin

<400> SEQUENCE: 14

Ser Pro Ser Gly Met Glu Arg Leu Tyr Gly Phe Gly Leu
1               5                   10

<210> SEQ ID NO 15
<211> LENGTH: 10
<212> TYPE: PRT
<213> ORGANISM: Artificial
<220> FEATURE:
<223> OTHER INFORMATION: Fusion protein of P. Americana Allostatin

<400> SEQUENCE: 15

Ala Asp Gly Arg Leu Tyr Ala Phe Gly Leu
1               5                   10

<210> SEQ ID NO 16
<211> LENGTH: 15
<212> TYPE: PRT
<213> ORGANISM: Artificial
<220> FEATURE:
<223> OTHER INFORMATION: Fusion protein of M. Sexta AST

<400> SEQUENCE: 16

Glu Val Arg Phe Arg Gln Cys Tyr Phe Asn Pro Ile Ser Cys Phe
1               5                   10                  15

-continued

```
<210> SEQ ID NO 17
<211> LENGTH: 18
<212> TYPE: PRT
<213> ORGANISM: Artificial
<220> FEATURE:
<223> OTHER INFORMATION: Fusion protein of D. Punctata

<400> SEQUENCE: 17

Ala Tyr Ser Tyr Val Ser Glu Tyr Lys Arg Leu Pro Val Tyr Asn Phe Gly Leu
1               5                   10                  15
```

FUSION PROTEINS FOR INSECT CONTROL

This application is a national stage application of PCT/GB02/03598, filed Aug. 6, 2002, which claims foreign priority to United Kingdom patent application 0119274.9, filed Aug. 8, 2001.

BACKGROUND OF THE INVENTION

1. Field of the Invention

The present invention relates to fusion proteins (FP) for mediating, in plants, protection against pathogens; and also means and methods for the production thereof. Moreover, the invention also relates to plant cells, plants, and their progeny, once transformed with constructs encoding the fusion proteins of the invention. Further, the invention also relates to pesticides including at least one fusion protein of the invention.

2. Description of the Related Art

Despite the wide range of pesticides that are available on the market plant disease is a major concern for farmers. Many pesticides are not sufficiently target specific and so result in environmental damage. What is more, even dispersion of pesticide may be difficult to achieve resulting in some crops being undesirably saturated with potentially toxic chemicals and some not receiving adequate protection.

Recent progress has exploited genetic techniques to engineer crops that have an in-built resistance to pathogens. These crops are advantageous because they dispense with the need to use conventional pesticides. Typically, the genetic code of crop plants is modified so that they express a protein that is toxic to at least one selected pathogen. More typically still, the protein is most likely to be effective when ingested by the pathogen and so targets the pathogen when it is at its most damaging. However, it has been found that once ingested by the pathogen these supposedly toxic proteins are degraded by the pathogen's digestive system and so rendered ineffective. There is therefore a need to design a protein that can resist this sort of defence.

We consider that pest management technologies based on insect neuropeptides offer a degree of biological activity, target specificity and environmental compatibility that are lacking in neurotoxic insecticides. However, to date, attempts to deliver such peptides by oral administration have proved unsuccessful. As mentioned, delivery via oral route would be optimal for insect crop protection since it would target the insect at its most damaging time. Accordingly it is thought advantageous to administer such peptides by spraying them on crops to be treated or engineering them into crops to be protected. But unfortunately these neuropeptides are susceptible to environmental degradation and, further, once ingested, they are broken down before they achieve their effect. They therefore need to be protected in some way.

Certain plant lectins show a low level of toxicity when incorporated into an artificial pathogen diet or when expressed in transgenic plants. Thus they are not thought to have any insecticidal properties. However, some have been shown to be resistant to gut proteolysis and can be found in the insect haemolymph following ingestion. Thus, we considered that plant lectins may have the potential to act as carrier members to deliver other peptides to the circulatory system of target species.

SUMMARY OF THE INVENTION

The object of the invention is therefore to provide a target specific pesticide which is suitable for oral delivery and resists degradation in the insect gut, and methods and means for its production and use in mediating plant disease resistance.

We have developed a novel fusion protein that is effective at destroying, or at least debilitating, plant pathogens. The protein comprises a, first, translocating member and a, second, toxic member. The translocating member aids passage of the toxic member through the pathogen gut and, ideally, into the insect haemolymph where the toxic member can realise its effects. We have discovered that plant lectins can be used to transport at least one toxic member through the insect gut. Further, we have found that, ideally, an insect peptide such as a neuropeptide can be used as the toxic member. Thus, when a plant protein is combined with an insect protein there is provided a novel fusion protein that is effective at mediating plant disease resistance.

BRIEF DESCRIPTION OF THE DRAWINGS

FIG. 1: Shows expression and purification of GNA (A) and GNA/Manse-AS (B) constructs in *E. coli*. Gels (A) and (B), lane 1 pre-induced culture; lane 2 IPTG induced culture; lane 3 lysate; lanes 4 & 5 flow through; lanes 6–9 in (A) and lane 6 in (B) are proteins purified by affinity chromatography; lane 10 in A and 7 in B native GNA. M, molecular mass marker (66, 45, 36, 29, 24, 20 & 14 kDa). Protein samples were resolved by 15% acrylamide SDS-PAGE gels.

FIG. 2: Shows detection of purified proteins by Western analysis using (A) anti-GNA and (B) anti-Manse-AS antibodies. Proteins were resolved by (A) 15% and (B) 20% acrylamide SDS-PAGE gels and electroblotted onto nitrocellulose. Loading as estimated by Bradford assay is as follows: (A) GNA lanes 1–4, 10, 25, 50, and 50 (unboiled) ng, respectively; lanes 5–8 GNA/Manse-AS, 10, 25, 50, and 50 (unboiled) ng, respectively, lanes 9 and 10 are GNA standards of 5 ng and 50 ng, respectively; (B) lanes 1–4 GNA/Manse-AS, 25, 50, and 50 (unboiled) ng, respectively. Arrows indicate monomeric and dimeric forms of GNA.

FIG. 3: (A) Shows mean increase/decrease in weight of *L. oleracea* larvae (% of pre-treatment weight; n=7) and (B) mean consumption (g wet weight artificial diet; n=7) following 24 h exposure to control; control+ammonia; recombinant GNA (1.5 mg/5 g diet)+ammonia; and recombinant GNA/Manse-AS (1.5 mg/5 g diet)+ammonia. Error bars show means +/− SE; probability values for significant differences between control and treatments are denoted (ANOVA).

FIG. 4: (A) Shows increase/decrease in mean wet weight of Vth instar *L. oleracea* larvae following exposure to control □ (n=8); control+ammonia □ (n=8); control+MeOH ■ (n=16); GNA (0.5 mg/5 g diet)+ammonia ▲ (n=8); Manse-AS (0.5 mg/5 g diet) in MeOH Δ (n=16); GNA+Manse-AS (0.5 mg/5 g diet) ♦ (n=8); and FP (0.5 mg/5 g diet) in ammonia ◇ (n=8); for 3 days. Error bars show means +/− SE; probability values for significant differences between FP and control treatments were significant (ANOVA) at $P<0.0001$ in all cases. (B) Total mean consumption per larvae (g wet wt artificial diet) for treatments in (A).

FIG. 5: Shows Manse-AS-like immunoreactivity in individual HPLC fractions of haemolymph (50 μg protein/sample) from Vth instar *L. oleracea* larvae fed on control (closed bars) and recombinant GNA/Manse-AS (0.1% w/w) (hatched bars) containing diets for 24 h. Arrows denote elution regions for standard recombinant FP and synthetic Mas.

DETAILED DESCRIPTION OF THE INVENTION

According to a first aspect of the invention there is provided a fusion protein comprising a translocating moiety and a toxic moiety wherein the translocating moiety comprises a plant protein that is capable of acting as a carrier to translocate the toxic moiety across the gut wall of at least one plant pathogen.

Reference herein to the term pathogen is intended to include reference to any insect that affects the growth, development, reproduction, harvest, yield or utility of a plant.

Suitably a toxic moiety comprises any agent, including its metabolic precursors or pro-agent, that affects the wellbeing, growth or reproduction of any pathogen and/or any stages of its life cycle, preferably is any biologically active toxic agent derived from insects or related arthropods, and metabolites and analogues thereof.

In a preferred embodiment of the invention the toxic agent is most effective following translocation and, ideally, is a natural or synthetic arthropod-derived peptide or protein or metabolite or analogue thereof, capable of causing deleterious effects on growth, development reproduction or mortality in pest insects; such as an insect or related arthropod or the like derived protein or peptide or neuropeptide or metabolite or analogue thereof, and most ideally an allatostatin, chitinase or diuretic hormone, metabolitic or analogue thereof.

Suitably the toxic agent is derived from insects such as cockroach, blowfly, mosquito, webworm, beetle, or related arthropods such as antipede, millipede, crab, lobster, shrimp, prawn, spider, scorpion, mite, tick and the like.

Suitable insect peptides for inclusion in the fusion protein include any one or more of the following neuropeptides and their natural or synthetic metabolites or analogues: *Manduca sexta* allatostatin (Manse-AS); cockroach allatostatin such as those found in either of the following species *Diplotera punctata* or *Periplaneta americana* or blowfly allatostatin such as in the species *Calliphora vomitaria*; alternatively insect specific enzymes can be used such as an insect chitinase for example, those found in *M. sexta; Bombyx mori*; the mosquito *Anopheles gambiae*; fall webworm *Hyphantria cunea*; beetle *Phaedon cochleariae*; or *Lacanobia oleracea*; alternatively, peptides comprising, or derived from, insect diuretic hormones such as those isolated from any one or more of the aforementioned species, or related arthropod hormones may be used. The choice for any given pesticidal composition or genetic transformation will be determined by the nature of the pathogen to be destroyed. For example, the size of the toxic agent will be chosen on the basis of the type of gut wall to be penetrated and the effectiveness of the toxic agent will be based on the type of insect to be destroyed.

Figure 5:
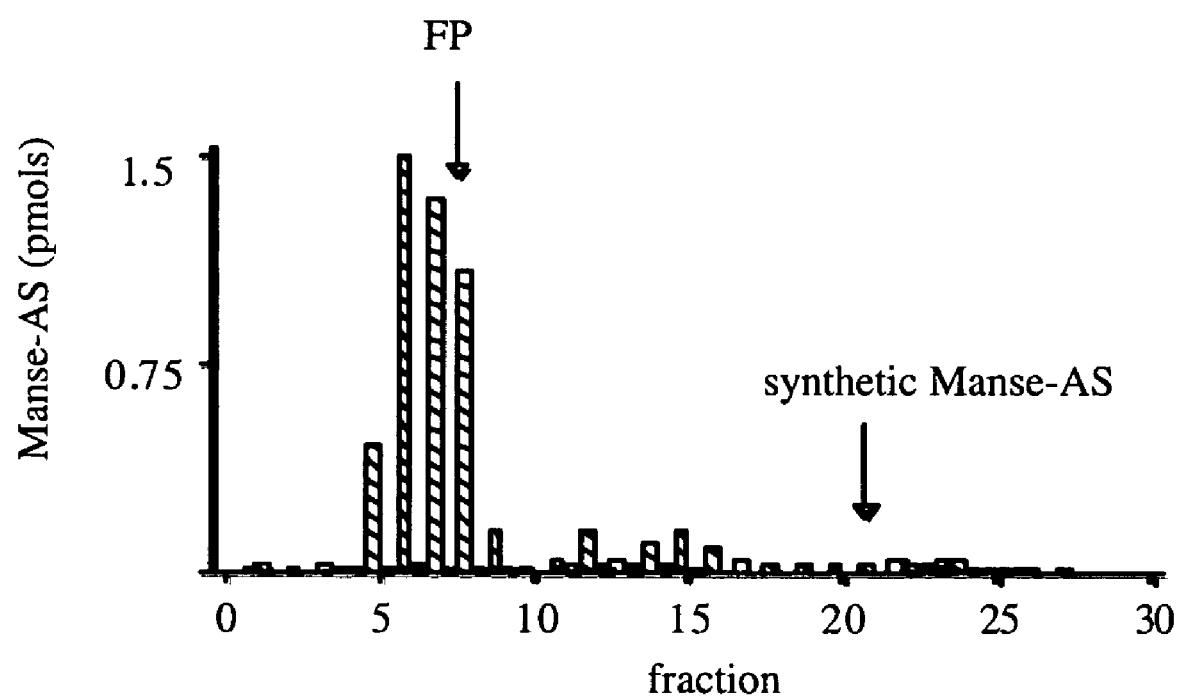

More ideally still said toxic agent is selected from the following group of toxic proteins and their metabolites and analogues: *Manduca sexta* Manse-AS (16, 17); *Diploptera punctata* allatostatin (38); *Periplaneta americana* allatostatin (39); *Calliphora vomitaria* allatostatin (40); or insect chitinase such as *M. sexta* chitinase (37, 34, 35); *Bombyx mori* chitinase (34, 37); *Anopheles gambiae* chitinase (36); *Hyphantria cunea* chitinase (34); *Phaedon cochleariae* chitinase (33) or *Lacanobia oleracea* chitinase; or insect diuretic hormone such as that isolated from *M. sexta* (32). Preferably a toxic agent in a fusion protein according to the invention comprises an insect protein as sequenced in the Table 2 and FIG. 5 (SEQ ID NO: 3–8, 14–17), and natural or synthetic metabolites or analogues thereof.

Suitable plant lectins for inclusion in the novel compound include any one or more of the following plant lectins: snowdrop lectin (GNA), pea lectin *Pisum sativum* (P-lec), peanut lectin *Arachis hypogaea*, french bean lectin (PHA, *phytohaemo glutinin*), and analogues thereof. These are just a few examples, generally any lectin that binds to insect gut can be used. The choice for any pesticidal composition or genetic transformation will be determined by the nature of the pathogen to be destroyed. For example, the type of lectin will be selected having regard to its stability in the insect gut, the type of gut wall to be penetrated and its level of toxicity; a non toxic lectin is preferred.

In a preferred embodiment of the invention said plant protein is selected from the following group of proteins: GNA (snowdrop lectin); P-lec pea lectin; or peanut lectin.

Preferably the moieties of the fusion protein are linked together by genetic or biochemical means and so, in the first instance, by at least one linking peptide or, in the second instance, by a covalent or non-covalent bond or linking moiety. Where a peptide is used to link said members together the number of peptides is determined by the distance between the relevant ends of each member when said fusion protein is in a biologically active conformation. The moieties may be releasably linked by means adapted to dissociate and release the toxic agent in situ in an insect gut, for example on metabolisation by the insect or may remain intact, depending on the active form of the toxic agent.

More preferably still the fusion protein is capable of destroying, or at least debilitating, any one or more classes of insect or related arthropods, for example any one or more of the following pathogens: Coleopterans eg. Southern corn rootworm (*Diabrotica undecimpunctata*); cowpea bruchid (*Callosobruchus maculatus*); Lepidopterans eg. European cornborer (*Ostinia nubilalis*); tobacco hornworm (*Manduca sexta*); stem borer (*Chilo partellus*): Homopteran pests eg. Rice brown plant hopper (*Nilaparvata lugens*); rice green leaf hopper (*Nephotettix cinciteps*); potato leaf hopper (*Empoasca fabae*); peach potato aphid (*Myzus persicae*). It will be apparent to those skilled in the art that many more pest species may be affected by the fusion protein of the invention, as will be apparent to those skilled in the art, and use of the fusion protein of the invention may be selected accordingly In yet a further preferred embodiment of the invention the fusion protein comprises the protein shown in (SEQ ID NO: 1) which is a combination of GNA (snowdrop lectin) and Manse-AS (*Manduca sexta* allatostatin).

According to a further aspect of the invention there is provided a pesticidal composition comprising the aforementioned fusion protein.

Preferably the composition as hereinbefore defined is in the form of any desired formulation such as a solution, emulsion, spray, suspension, powder, foam, paste, granule, aerosol, capsule or other finely or coarsely divided material or impregnant for natural or synthetic material.

In a preferred embodiment said pesticidal composition is in the form of a spray, suspension or the like, in admixture with suitable diluents, adjuvants, preservatives, dispersants, solvents, emulsifying agents or the like. Suitable composition components are those conventionally employed in the art, and in particular being suited to the present oral administration application. The composition may be obtained with use of any suitable solvents, preferably water, alcohol, mineral oil or the like, any suitable solid carriers such as kaolin, clay, talc, chalk, quartz, attapulgite, montmorillonite, diatomaceous earth, silica, or the like, with use of any solid carriers as supports for granules such as calcite, marble, pumice and crushed natural fibre material or the like. Compositions for use in the invention may additionally be employed in intimate or physical admixture together with other known insecticides, growth promoting or regulating substances, herbicides, fungicides, synergistic agents and the like.

The composition is preferably suitable for physically or chemically associating with plants or their locus, and for oral uptake by pathogens.

The composition may therefore comprise a fusion protein as hereinbefore defined in an amount of between 0.1 and 99% by weight, preferably between 0.5 and 98% by weight, more preferably between 1.0 and 95% by weight.

In a further aspect of the invention there is provided a method for administering a composition as hereinbefore defined to a plant or its locus for combatting insect pests.

Preferably 0.1 to 5 g, more preferably 0.2 to 4 g of the composition are applied per $m^2$ of plant surface area to be treated, such as seed or leaf surface area to be coated, providing pesticidal activity for a period of 24 hours to 2 weeks, for example for a period of 1 week to 2 weeks.

In a further aspect of the invention there is provided a process for the preparation of a composition as hereinbefore defined which comprises the admixture of an amount of a fusion protein and carrier as hereinbefore defined, adapted for the oral administration of an effective pesticidal amount of a fusion protein as hereinbefore defined, in intimate admixture with diluents, adjuvants, preservatives, dispersants, solvents, emulsifying agents and the like as hereinbefore defined.

In a further aspect of the invention there is provided a process for the preparation of a fusion protein as hereinbefore defined by biochemical or chemical synthesis, expression, coupling, or modification. Suitably any techniques for preparing proteins may be employed.

According to a further aspect of the invention there is provided a polynucleotide encoding the aforementioned fusion protein.

In a preferred embodiment of the invention said polynucleotide comprises that shown in (SEQ ID NO: 1) or an effective fragment thereof.

According to a further aspect of the invention there is provided a vector comprising the aforementioned polynucleotide. Alternatively, there is provided at least one vector encoding two separate polynucleotides wherein each polynucleotide encodes a different member of said fusion protein or, ideally, two vectors each encoding one of said separate polynucleotides.

Preferably, in the instance where said two separate polynucleotides are provided they are supplemented with means for enabling self assembly of the fusion protein in vivo. For example, each polynucleotide is provided with a complementary binding domain whereby the said polynucleotides can be linked together, pre or post translationally, to form a functional fusion protein. Said complementary binding domains are well know to those skilled in the art and may comprise homo- or hetero-binding partners such as leucine zippers or antibody/antigen fragments, respectively.

In a preferred embodiment of the invention said polynucleotide(s) is/are operatively linked to regulatory sequences allowing expression of said fusion protein in a host cell. Preferably said regulatory sequences are constitutative, tissue specific or inducible promoters. Preferably also said regulatory sequences may comprise a transcription termination signal, such as a poly-A signal. Additionally, said polynucleotides are ideally provided with a secretion signal whereby expression of same in a host cell results in secretion of said fusion protein, or members thereof, into the culture medium of said host cell.

Preferably said vector(s) comprise plasmids, cosmids, viruses, bacteriophages or other vectors used in genetic engineering.

According to a further aspect of the invention there is provided a host cell comprising the aforementioned polynucleotide(s) and/or vector(s).

Preferably, in the instance where two vectors are used, said host cell is cotransformed with same. Alternatively, those skilled in the art may prefer to use conventional sexual crossing to produce a hybrid expressing both members of the fusion protein.

Preferably said vector is integrated into the genome of the host cell and most ideally stably integrated into said genome. Alternatively, said vector is maintained extrachromosomally.

Preferably said host cell is prokaryotic or eukaryotic such as bacterial, insect, fungal, plant or animal and in each case said regulatory sequences are adapted accordingly to enable expression of said polynucleotide(s) in said host species. For example, where said host cell is a plant cell, said regulatory sequence comprises a promoter active in plant cells, such promoters are well known to those skilled in the art and just one example is the promoter of the polyubiquitin gene of maize. Alternatively a tissue specific promoter may be used such as those active in the tubers of potatoes or in seeds of different plants.

According to a preferred embodiment of the invention there is provided a method for the production of the aforementioned fusion protein comprising:

culturing the aforementioned host cell under conditions suitable for expression of said fusion protein; and harvesting said fusion protein from said culture.

In the instance where said host cell comprises at least one vector encoding the two separate polynucleotides said polynucleotides are supplemented with binding domains that provide for self assembly of said fusion protein in vivo.

According to a further aspect of the invention there is provided a method for the production of transgenic plant cells or plants that are resistant to disease comprising:

transforming a selected plant genome with the aforementioned vector(s) of the invention.

According to a yet further aspect of the invention there is provided a transgenic plant cell or plant, or their progeny, produced by the above method.

Preferably said plant, cell or its progeny is either a monocotyledon or a dicotyledon. Ideally said plant is a crop plant such as maize, rice potato, tomato or sorghum.

According to a yet further aspect of the invention there is provided a transgenic plant cell or plant, or their progeny, including in its genome a polynucleotide encoding either the fusion protein of the invention or a member thereof.

In a preferred embodiment of the invention said polynucleotide is stably integrated into the genome. Alternatively said polynucleotide is maintained extrachromosomally.

Preferably said plant, cell or its progeny is either a monocotyledon or a dicotyledon. Ideally said plant is a crop plant such as maize, rice, potato, tomato, or sorghum.

According to a further aspect of the invention there is provided the use of the aforedescribed fusion protein in the manufacture of a pesticide or a transgenic plant cell or plant.

According to a yet further aspect of the invention there is provided the use of the aforementioned pesticide to destroy, or debilitate any one or more of the pathogens as hereinbefore defined.

An embodiment of the invention will now be described, by way of example only, with reference to the following figures wherein:

SEQ ID NO: 1 and 2 show the nucleotide and deduced amino acid sequences of the fusion protein GNA/Manse-AS and GNA constructs showing restriction sites introduced by PCR for cloning into pET14b. The position of GNA, linker and Manse-AS fragments are shown for GNA/Manse-AS (.) denotes stop codon in the GNA sequence.

Abbreviations: GNA, *Galanthus nivalis* agglutinin; Manse-AS, *Manduca sexta* allatostatin; FP, recombinant GNA/Manse-AS fusion protein; Vth, fifth; MeOH, methanol.

Materials and Methods

Materials and Recombinant DNA Techniques.

Standard GNA was obtained from Vector Laboratories Inc. (USA) and synthetic Manse-AS was prepared by the Advanced Biotechnology Centre (Charing Cross and Westminster Hospital Medical School, London). Anti-GNA and anti-Manse-AS antibodies, raised in rabbits, were prepared by Genosys Biotechnologies (EUROPE), Cambridge, UK.

Subcloning was carried out using the TOPO cloning kit (pCR2.1 TOPO vector) purchased from Invitrogen. Expression vector pET14b, competent Novablue and expression host BL21 (DE3)pLysS cells were from Novagen. A cDNA sequence encoding for the mature peptide LECGNA2, one of several GNA isoforms (supplied by Dr. E van Damme; 28), was used as a template for PCR amplification. Oligonucleotide primers were synthesised by MWG Biotech (Ebersberg, Germany) and are listed in Table 1. PCR reactions were carried out using Pfu DNA polymerase (Promega) as described by the enzyme supplier. Plasmid DNA was prepared using Promega Wizard miniprep kits. Restriction endonucleases were obtained from Boëhringer Ltd, T4 Polynucleotide kinase and T4 DNA ligase were from Promega. PCR amplified fragments were sequenced by the Department of Biological Sciences, University of Durham, UK.

pCR2.1 TOPO vector and subject to sequence analysis. Plasmid DNA was digested with Nde I and Bam HI, gel purified and ligated to digested pET14b DNA to generate the plasmid MODGNA(A)109pET14b. Following isolation from transformed Novablue cells, the plasmid was transformed into BL21(DE3)pLysS cells.

A GNA/Manse-AS fusion construct was prepared by amplification of the mature GNA coding sequence from LECGNA2 cDNA using the primers 5'GNA/Nde I and 3'GNA Bam HI (SEQ ID NO: 9 and 10) (Table 1), gel purified and ligated to digested pET14b DNA. This plasmid MODGNA(B)pET14b was digested with Bam HI and gel purified in preparation for ligation of a double stranded (ds) Manse-AS and linker peptide fragment. Single stranded (ss) oligonucleotides 5' Manse-AS and 3' Manse-AS (SEQ ID NO: 12 and 13) (Table 1) were designed using the published sequence for the *M. sexta* Manse-AS peptide (16) and the *Pseudaletia unipunctata* Manse-AS neuropeptide (NCBI gb/U36570/PUU36570) (17). 5' and 3' Manse-AS primers (SEQ ID NO: 12 and 13) contained Bam HI overhangs to facilitate ligation into Bam HI digested MODGNA(B) pET14b. An additional 12 oligonucleotides preceeding the Manse-AS sequence encode for a linker peptide. A ds Manse-AS fragTnent was generated by combining 300 pmols each of ss 5' Manse-AS and 3' Manse-AS (SEQ ID NO: 12 and 13) in the presence of ligase buffer. The mix was heated to 90° C., cooled to 30° C., and then incubated at 37° C. for 30 min in the presence of 1U T4 Polynucleotide kinase, 2.5 mN ATP and kinase buffer. DNA was phenol extracted and quantitated by spectrophotometry. Ligation mixes containing GNAMOD109(B)pET14b, ds Manse-AS and ligase buffer were heated to 80° C. and left to cool to 37° C. before 0.5 U T4 DNA ligase was added and the mix incubated at 4° C. overnight. Following isolation of the plasmid from transformed Novablue cells, colony PCR (using 5' GNA/Nde I and 3' Manse-AS primers (SEQ ID NO: 9 and 13)) was performed to isolate transformants containing the GNA/Manse-AS fragment in the correct orientation. Selected transformants were sequenced prior to transformation into BL21(DE3)pLysS cells.

For protein overproduction BL21(DE3)pLysS GNA and GNA/Manse-AS were cultivated with shaking at 37° C. in 1 L of LB broth containing 50 μg/ml carbenicillin and 34

TABLE 1

Oligonucleotide primers

| Primers | Sequence | | |
|---|---|---|---|
| 5'GNA/Nde I | TAATCATATGGACAATATTTTGTACTCC | (28 mer) | (SEQ ID NO: 9) |
| 3'GNA/BAC109 | ATTAGGATCCTCATCCGGTGTGAGTTCCAG | (30 mer) | (SEQ ID NO: 10) |
| 3'GNA/Bam HI | TAATGGATCCGGTGTGAGTTCCAG | (24 mer) | (SEQ ID NO: 11) |
| 5' Manse-AS | GATCCGGGGGCATATGCAGGTGCGCTTCCGC CAGTGCTACTTAACCCCATCTCCTGCTTCTGAG | (65 mer) | (SEQ ID NO: 12) |
| 3' Manse-AS | GATCCTCAGAAGCAGGAGATGGGGTTGAAGTAG CACTGGCGGAAGCGCACCTGCATATGCCCCCCG | (66 mer) | (SEQ ID NO: 13) |

Cloning, Expression and Purification of GNA and GNA/Manse-AS Constructs.

The mature GNA coding sequence (109 residues) was amplified from LECGNA2 cDNA using the primers 5'GNA/Nde I and 3'GNABAC109 (SEQ ID NO: 9 and 10) (Table 1). The gel purified PCR product was subcloned into the μg/ml chloramphenicol. Cultures were induced with 0.4 mM isopropyl beta-D-thiogalactoside when an O.D. of 0.6–0.7 had been attained. Cultivation at 37° C. was continued for 3 h post induction. Cells were harvested by centrifugation (30 min at 6000×g) and re-suspended in 100 ml binding buffer (20 mM Tris, 0.5 M NaCl, 5 mM imidazole, 6 M urea, pH 7.8). Cells were lysed by sonication and cellular debris removed by centrifugation (20 min at 10000×g). Recombinant GNA and GNA/Manse-AS were purified by affinity chromatography using Ni-NTA Superflow resin (Qiagen). Columns (5 ml) loaded at 1 ml/min were washed with wash buffer (20 mM Tris, 0.5 M NaCl, 20 mM imidazole, 6 M urea, pH 7.8) and bound protein eluted with elution buffer (20 mM Tris, 0.5 M NaCl, 0.3 M imidazole, 6 M urea, pH 7.8). Purified GNA and GNA/Manse-AS fractions were diluted to 10–50 µg/ml, based on SDS-PAGE estimations of concentration, in 20 mM Tris, 4 M urea, pH 7.8, and dialysed sequentially against 20 mM Tris, 1 M urea, pH 7.8 and dH2O (containing approx. 0.01% ammonium bicarbonate). After dialysis renatured proteins were filtered (0.45 µM Nalgene, BDH), frozen in liquid nitrogen and freeze-dried.

Haemagglutination Assays.

Freeze dried GNA and FP re-suspended in dH2O, with the addition of small amounts of 0.1% (v/v) ammonia to aid solubilisation where necessary, were analysed for activity by agglutination assays using native GNA as a standard. The concentration of recombinant proteins were estimated by a microtitre based Bradford Assay (Biorad) using native GNA as the standard protein. Haemagglutination assays were carried out as described (29), except that a total volume of 50 µl (25 µl aliquots of serial twofold dilutions of lectins and 25 µl of 2% erythrocyte suspension) was used in each well. Following incubation for 2 h at room temperature the lowest concentration required to completely agglutinate the red blood cells was determined visually. Concentration and reactivity with anti-GNA and anti-Manse-AS antibodies was verified as previously described for GNA (30) by Western blotting.

Insects.

*Lacanobia oleracea* were reared continuously on artificial diet (31) at 25° C. under a 16:8 L:D regime.

Insect Bioassays.

A potato leaf based artificial diet (24) was used to assay recombinant proteins against newly moulted Vth stadium *L. oleracea* which were starved for 24 h prior to exposure to diets. To encourage feeding, sucrose was incorporated at 0.05% (w/w) in assays 2 A and B and at 0.5% (w/w) in assay 3. Individual larvae were maintained in clear plastic pots containing moist filter paper to prevent diet desiccation. Larval wet weights (−/+0.1 mg) were recorded before, during, and after exposure to treatments, and diet consumption was estimated on a wet weight basis. The amounts of recombinant proteins added to diets were based on activity values derived from agglutination assays.

Bioassay 1.

Larvae (n=7 per treatment) were exposed to control diet; control diet containing ammonia (0.0002 v/w); diet containing recombinant GNA at a concentration of approx. 1.5% (w/w) of dietary protein (1.5 mg/5 g diet wet weight) and diet containing recombinant FP at a concentration of approx. 1.5% (w/w) of dietary protein for 24 h.

Bioassay 2A.

Larvae (n=8 per treatment) were exposed for 3 days to control diet; control diet containing ammonia; diet containing native GNA at approx. 0.5% (w/w) of dietary protein; diet containing native GNA and synthetic Manse-AS at a total concentration of approx. 0.5% (w/w) (i.e. ratio of GNA: Manse-AS equivalent to FP and diet containing FP at approx. 0.5% (w/w) of dietary protein.

Bioassay 2B.

Larvae (n=16 per treatment) were exposed for 3 days to diet containing synthetic Manse-AS (re-suspended in 70% MeOH) at a concentration of 0.5% (w/w) of dietary protein and a control diet containing an equivalent volume of MeOH.

Bioassay 3.

Larvae (n=20 per treatment) were exposed to control diet containing ammonia; diet containing native GNA and synthetic Manse-AS (at a total concentration of approx. 0.1% (w/w)); diet containing synthetic Manse-AS (at a concentration equivalent to FP at 0.1% (w/w)) and diet containing FP at a concentration of approx. 0.1% (w/w) of dietary protein. Haemolymph samples were extracted after 24, 48 and 72 h of exposure to the diets in the following manner. Pre-chilled larvae were blotted with EtOH and dried prior to haemolymph extraction, carried out by piercing the cuticle with a fine needle. Haemolymph was placed into pre-chilled eppendorfs containing phenylthiocarbamide-phenol oxidase inhibitor. Protein concentrations of pooled samples for each time point were estimated using a microtitre plate-based Bradford Assay with BSA as the standard protein.

Indirect ELISA.

Aliquots of extracts from bioassay 3 were analysed for the presence of Manse-AS using an indirect enzyme linked immunosorbent assay (ELISA), as previously described (18).

Haemolymph HPLC Purification and Immunoassay.

Aliquots of haemolymph extracted from larvae in bioassay 3 exposed to control and FP containing diets for 24 h were further analysed for the presence of Manse-AS-like immunoreactivity in the following manner: samples were sonicated in 200 µl ice cold 60% acetontrile, centrifuged at 12,000×g at 4° C. for 20 mins, and the supernatant diluted 10 fold with 0.1% TFA. This was loaded onto a custom made preparative cartridge (100 mg $C_4$ RP packing; Bondapak, Waters). The cartridge was eluted with 1 ml each of 20% and 60% $CH_3CN$/0.1% TFA and the 60% fractions were concentrated to 100 µl by centrifugal evaporation for ELISA, or further purification by HPLC.

Chromatography was performed using a Beckman System Gold chromatographic system, utilising a dual pump programmable solvent module 126. Samples were loaded via a Rheodyne loop injector onto a spherogel-TSK G2000Sw gel filtration column (10µ, 7.5×300 mm). The column was eluted with 0.1 M phosphate buffer over 30 min at a flow rate of 1 ml/min, and elutions monitored at 220 nm by a System Gold diode array detector module 168. Fractions (1 ml) were collected and dried down by centrifugal evaporation for immunoassay. Synthetic Manse-AS and FP were also subjected to Gel filtration chromatography to determine their elution positions.

Statistical Analysis.

All data analysis was carried out using the Statview (v. 4.5; Abacus Concepts, Berkely, Calif. USA) software packages on Apple Macintosh computers. ANOVA analysis was carried out to determine any significant differences between treatments in the parameters measured. The acceptance level of statistical significance was $P<0.05$ in all instances.

Results.

Two constructs encoding for GNA and a GNA/Manse-AS fusion protein (SEQ ID NO: 2 and 1) were prepared and cloned into the expression vector pET14b which carries a N-terminal Histidine purification tag. Constructs in BL21

Figure 2:
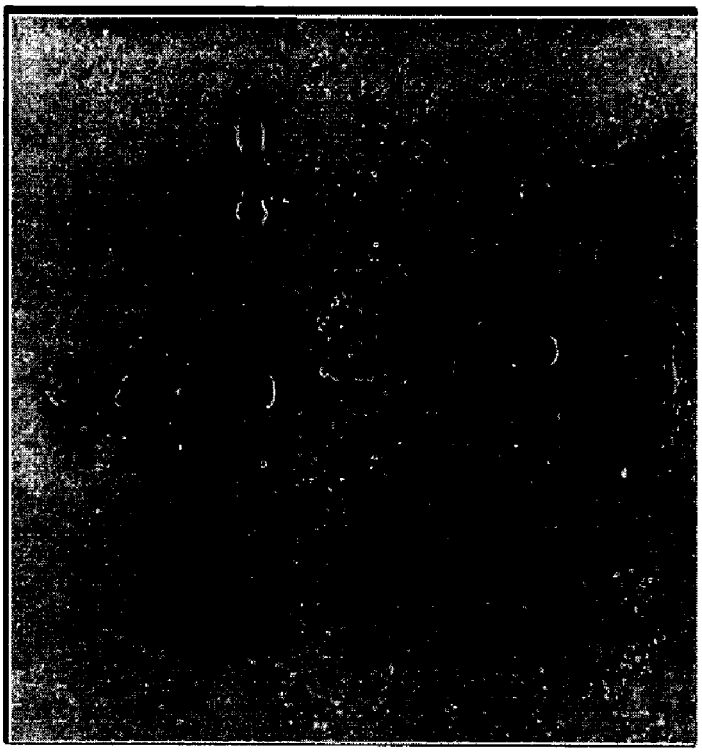
Figure 2:
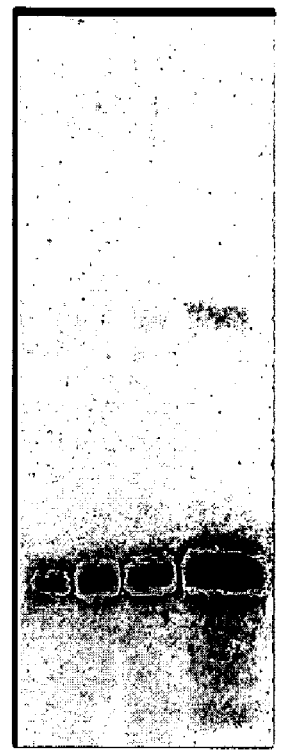
Figure 3:
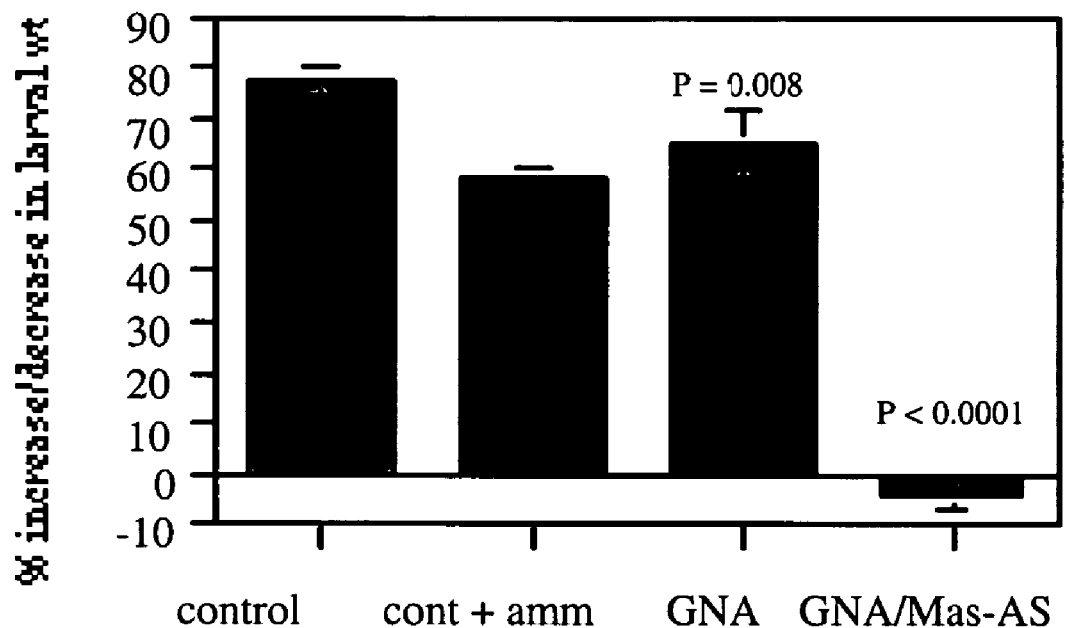
Figure 3:
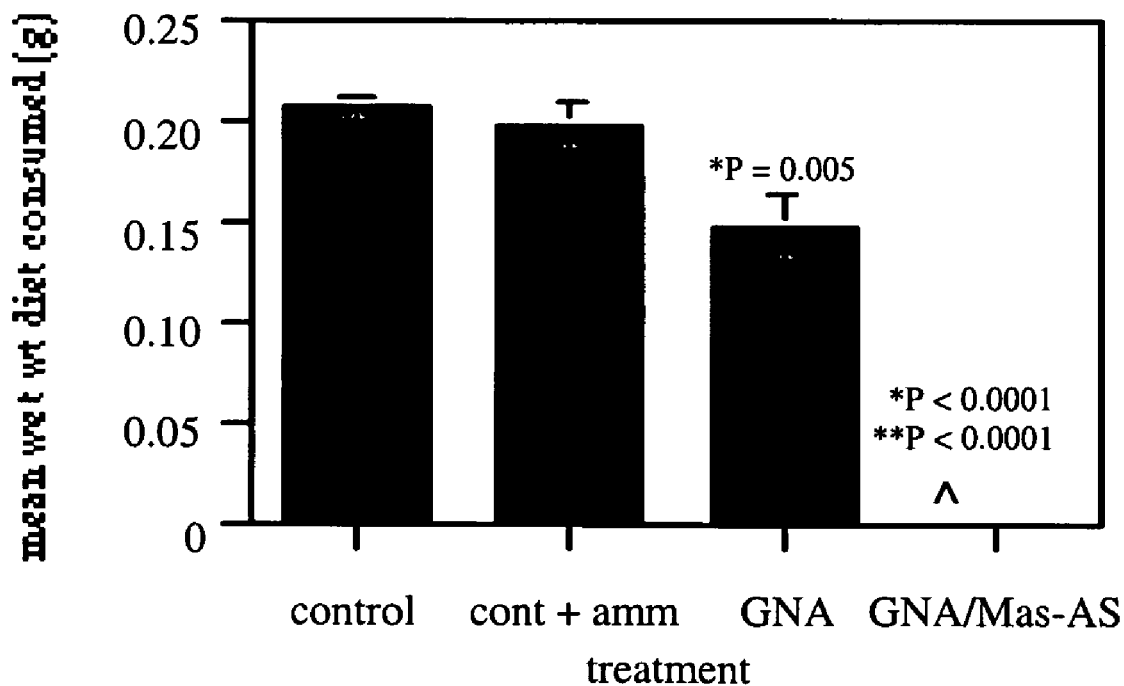

(DE3)pLysS overexpressed well (10–15 mg/L culture), and both proteins accumulated as insoluble inclusion bodies that were purified to >90% homogeneity by a single affinity purification step (FIGS. 1A & B). Western analysis of purified GNA and FP (FIGS. 2A & B) confirmed that both proteins reacted positively with anti-GNA antibodies and FP with anti-Manse-AS antibodies. Following purification and renaturation steps yields for both proteins were estimated at 1–5 mg/L of culture.

Figure 4:
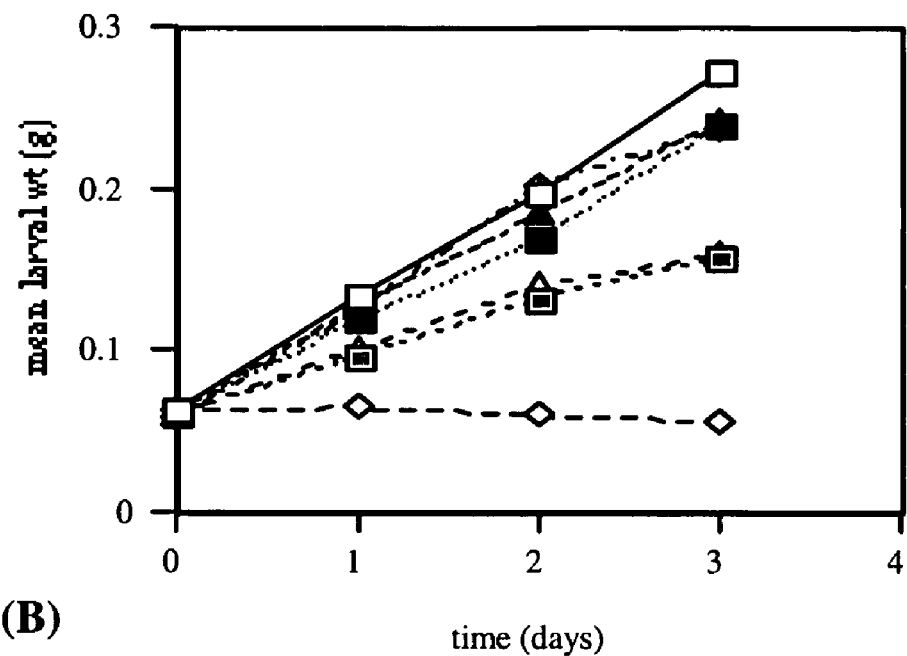
Figure 4:
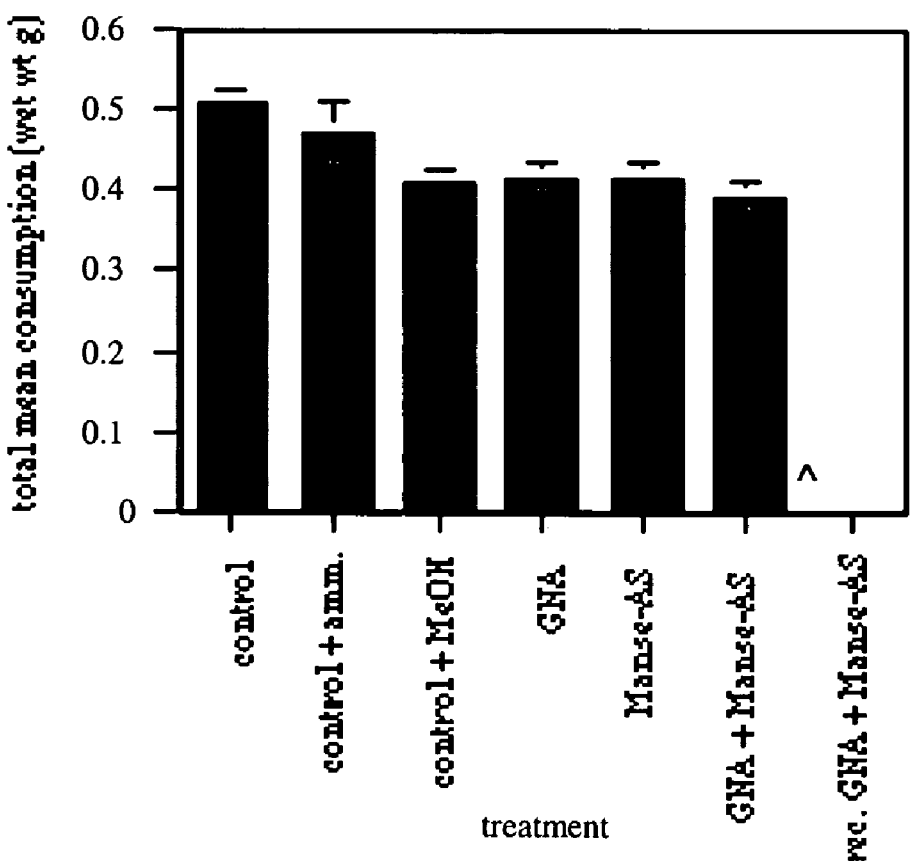

When exposed to diet containing FP at 1.5% of dietary protein L. oleracea larvae exhibited a significant reduction (ANOVA: P<0.0001) in weight (FIG. 4A). In contrast a more than 50% increase in mean weight was observed for larvae fed on control and recombinant GNA (1.5% total dietary protein) diets over the 24 h assay period. That the significant reduction in weight of larvae exposed to FP was due to minimal feeding was confirmed by measurements of diet consumption depicted in FIG. 4B. Whilst there was some evidence for feeding (indicated by the presence of diet in the guts of dissected larvae) consumption was too low to give a value by wet weight analysis.

In a second assay Vth instar larvae were exposed to FP at 0.5% of dietary protein for 3 days. Larval weight and consumption values recorded over the assay period were combined with results obtained in a third assay (2B) where larvae were exposed to synthetic Manse-AS (at 0.5% of dietary protein) and are presented in FIGS. 5A and B. As observed in assay 1, all larvae exposed to diet containing FP exhibited a significant reduction in weight (ANOVA: P<0.0001) whereas insects fed on control diet or diet containing GNA or a combination of native GNA and synthetic Manse-AS, showed a fourfold increase in weight over the assay period. Similar values obtained for insects fed on diet containing synthetic Manse-AS (0.5% w/w in MeOH) and control diet containing an equivalent volume of MeOH indicated that it was the presence of MeOH, rather than Manse-AS, that was responsible for the depressed growth rate of these replicates shown in FIG. 5A. The consumption of diet by insects (FIG. 5B) equated with larval growth represented by FIG. 5A. As observed in assay 1, evidence of feeding by FP exposed larvae was apparent only by the presence of diet in dissected larval guts.

A Manse-AS-like immunoreactivity in HPLC fractions of haemolymph from control and FP fed larvae is shown in FIG. 6. There was very little Manse-AS-like immunoreactivity in control samples. In contrast, significant amounts of Manse-AS-like immunoreactivity were observed in fractions from FP fed larvae in a region (between 5 and 9 mins) that co-eluted with synthetic FP. By comparison no significant Manse-AS-like immunoreactivity was observed to co-elute with synthetic Manse-AS.

Discussion

A novel fusion protein combining snowdrop lectin (GNA) and an insect neuropeptide allatostatin (Manse-AS) has been expressed in E. coli and purified. This fusion protein has been delivered intact to the blood of exposed insects.

The incorporation of FP at 1.5% and 0.5% of proteins in diet was seen to have a dramatic effect upon growth and food consumption by Vth instar L. oleracea larvae. Larvae exposed to FP at 1.5% of dietary proteins exhibited a significant reduction in weight compared to a more than 50% weight gain observed for control and GNA-fed larvae over a 24 h period. Similarly larvae exposed to FP at 0.5% of dietary proteins showed a significant reduction in weight over a period of 3 days whereas control and GNA-fed larvae exhibited a four fold increase in weight. That this was an antifeedant effect was demonstrated by minimal consumption of FP containing diets.

That the observed toxicity FP was due to the biological activity of the fusion protein was indicated by the significant differences observed in larval growth and food consumption between the various control treatments and FP treatments in both assays.

Antifeedant effects observed in the present study, together with the identification of Manse-AS-like immunoreactivity in the haemolymph of exposed insects, suggest that Manse-AS, delivered to the haemolymph by GNA, is exerting an inhibitory effect upon larval feeding. There exists a clear potential for fusion proteins of this type to exert significant insecticidal effects if the antifeedant properties observed in this study are commercially exploited.

TABLE 2

| | |
|---|---|
| *P Americana* allatostatin | |
| Pea AST1-H-Ser-Pro-Ser-Gly-Met-Glu-Arg-Leu-Tyr-Gly-Phe-Gly-Leu-NH2 | (SEQ ID NO: 14) |
| Pea AST2-H-Ala-Asp-Gly-Arg-Leu-Tyr-Ala-Phe-Gly-Leu-NH2 | (SEQ ID NO: 15) |
| *M Sexta* AST | |
| pGlu-Val-Arg-Phe-Arg-Gln-Cys-Tyr-Phe-Asn-Pro-Ile-Ser-Cys-Phe-OH | (SEQ ID NO: 16) |
| *D. punctata* | |
| Ala-Tyr-Ser-Tyr-Val-Ser-Glu-Tyr-Lys-Arg-Leu-Pro-Val-Tyr-Asn-Phe-Gly-Leu-NH2 | (SEQ ID NO: 17) |

REFERENCES

16. Kramer, S. J., Toschi, A., Miller, C. A. Kataoka, H., Quidstad, G. B., Li, J. P., Carney, L. & Schooley, D. A. (1991) *Proc. Natl. Acad. Sci.* USA, 88, 9458–9462.

17. Jansons, I. S., Cusson, M., Mcneil, J. N., Tobe, S. S., Benedena, W. J. (1996) *Insect Biochem. Molec. Biol.* 26 (3), 767–773.

18. Audsley, N., Weaver, R. J. & Edwards, J. P. (1998) *Insect Biochem. & Mol. Biol.* 28, 775–784.

24. Fitches, E., Gatehouse, A. M. R. & Gatehouse, J. A. (1997) *J. Insect Physiol.* 43(8), 727–739.

28. Van Damme, Els., J. M., Norbert De Clerq, Claessens, F., Hemscoote, K., Peeters, B., Peumans, W. J. (1991) *Planta* 186, 35–43.

29. Raemaekers, R. J., Laura de Muro, Gatehouse, J. A., Fordham-Skelton, A. P. (1999). *FEBS,* 265, 394–403.

30. Fitches, E., & Gatehouse, J. A. (1998) *J. Insect Physiol.* 44, 1213–1224.
31. Bown, D. P., Wilkinson, H. S., Gatehouse, J. A. (1997) *Insect Biochem & Mol. Biol.* 27 (7), 625–638.
32. Maeda, S. (1989) Biochemical & Biophysical Res. Comm. Vol 165, No. 3, p1177–1183.
33. Girard, C., Jouain, L. (1999) Insect Biochemistry & Molecular Biology 29, p549–556.
34. Kim, M. G., Shin, S. W., Bae, K. S., Park, H. Y. (1998) Insect biochemistry & Molecular Biology 28, p163–171.
35. Kramer, K. L., Muthukrishnan, S. (1997) Insect Biochemistry & Molecular Biology 27, 887–900.
36. Shen, Z., Jacobs-Lorena, M. (1997) Journal of Biological Chemistry, Vol 272, No. 46, p28895–28900.
37. Babiker, M. A., Banat, A., Kameyama, Y., Yoshioka, T., Koga, D. (1999) Insect Biochemistry & Molecular Biology 29, p537–547.
38. Pratt G E et al, Proc Natl Acad Sci USA, Vol 88, 2412–2416 Biochemistry (1991)
39. Weaver R J et al, Comp Biochem Physiol Vol 107C, 119–127 (1994)
40. Duve H et al, Proc Natl Acad Sci USA Vol 90, 2456–2460 Biochemistry (1993)

The invention claimed is:

1. A fusion protein comprising a translocating moiety and a toxic moiety, wherein the translocating moiety contains a plant lectin capable of acting as a carrier to translocate the toxic moiety across the gut wall of at least one plant pathogen, and wherein the toxic moiety is adapted to be effective as a toxic agent following translocation, and wherein said toxic agent is a natural or synthetic pest-insect-derived or related arthropod-derived peptide or protein or neuropeptide or metabolite or analogue thereof, said toxic agent being capable of causing deleterious effects in the nervous system, circulatory system or endocrine systems in pest insects or related arthropods.

2. A fusion protein as claimed in claim 1 wherein said toxic agent is an allatostatin, chitinase, diuretic hormone, or a metabolite or an analogue thereof.

3. A fusion protein as claimed in claim 1 wherein said toxic agent is derived from insects selected from the group consisting of cockroach, blowfly, mosquito, webworm, and beetle, or from antipede, millipede, crab, lobster, shrimp, prawn, spider, scorpion, mite, or tick.

4. A fusion protein as claimed in claim 1 wherein insect peptides for inclusion in the fusion protein are selected from the group consisting of the following neuropeptides and their natural or synthetic metabolites or analogues: *Manduca sexta* allatostatin (Manse-AS); cockroach allatostatin including those found in *Diplotera punctata* or *Periplaneta americana*; or blowfly allatostatin found in the species *Calliphora vomitaria*.

5. A fusion protein as claimed in claim 1 wherein a toxic agent is selected from the following group of toxic proteins and their metabolites and analogues: *Manduca sexta* Manse-AS; *Diploptera punctata* allatostatin; *Periplaneta americana* allatostatin; *Calliphora vomitaria* allatostatin; insect chitinase including *M. sexta* chitinase; *Bombyx mori* chitinase; *Anopheles gambiae* chitinase; *Hyphantria cunea* chitinase; *Phaedon cochleariae* chitinase, *Lacanobia oleracea* chitinase; or insect diuretic hormone including that isolated from *M. sexta*.

6. A fusion protein as claimed in claim 1 wherein said toxic agent is selected from an insect protein selected from the group consisting of SEQ ID NOS: 3–8 and 14–17, and natural or synthetic metabolites or analogues.

7. A fusion protein as claimed in claim 1 wherein said plant lectin is selected from any one or more of the following plant lectins: snowdrop lectin (GNA), pea lectin *Pisum sativum* (P-lec), peanut lectin *Arachis hypogaea*, French bean lectin (PHA, phytohaerno glutinin), and analogues thereof.

8. A fusion protein as claimed in claim 1 wherein the moieties of the fusion protein are capable of being linked together by genetic or biochemical means, said genetic means including being linked together by at least one linking peptide, and said biochemical means including being linked together by a covalent or non-covalent bond or linking moiety.

9. A fusion protein as claimed in claim 1 which is capable of destroying, or debilitating, an insect or related arthropod, selected from: Coleopterans, Lepidopterans and Homopteran pests.

10. A fusion protein as claimed in claim 9 wherein said insect or related arthropod is a coleopteran selected from Southern corn rootworm (*Diabrotica undecimpunctata*) or cowpea bruchid (*Callosobruchus maculatus*).

11. A fusion protein as claimed in claim 9 wherein said insect or related arthropod is a lepidopteran selected from European cornborer (*Ostinia nubilalis*), tobacco hornworm (*Manduca sexta*) or stem borer (*Chilo partellus*).

12. A fusion protien as claimed in claim 9 wherein said insect or related arthropod is a homopteran selected from Rice brown plant hopper (*Nilaparvata luigens*), rice green leaf hopper (*Nephotettix cinciteps*), potato leaf hopper *Empoasca fabae*) or peach pottoe aphid (*Myzus persicae*).

13. A fusion protein as claimed in claim 1 which comprises the protein of SEQ ID NO:1 which is a fusion of GNA (snowdrop lectin) and Manse-AS (*Manduca sexta* allatostatin).

14. A fusion protein as claimed in claim 1 wherein the insect peptides for inclusion in said fusion protein are selected from the group consisting of the following insect-specific enzymes: an insect chitinase, including those found in *M. sexta; Bornbyx mori*; the mosquito *Anopheles garnbiae*; fall webworm *Hyphantria cunea*; beetle *Phaedon cochleariae*; or *Lacanobia oleracea*.

15. A fusion protein as claimed in claim 1, wherein the insect peptides for inclusion in the fusion protein are selected from the group consisting of the following peptides comprised or derived from insect diuretic hormones including insect diuretic hormones isolated from any one or more of the following insect species: *Diplotera punctata, Periplaneta americana, Calliphora vomitaria, M. sexta, Bormbyx mori, Anopheles gambiae, Hyphantria cunea, Phaedon cochleariae, Lacanobia oleracea*, or related arthropod hormones.

16. The fusion protein of claim 1, wherein said toxic agent is derived from spiders.

17. The fusion protein of 16, wherein said toxic agent includes Atracotoxin-hvI, Hanatoxin 1, Huwentoxin-I, omega-Agatoxin, Phrixotoxin 1, and Robustoxin.

18. The fusion protein of claim 1, wherein said toxic agent is derived from scorpions.

19. The fusion protein of claim 18, wherein said toxic agent includes charybdotoxin, CsE-V, AaHIT4, Tityustoxin-VII, and CssII toxin.

20. A pesticidal composition comprising a fusion protein as claimed in claim 1 in the form of a solution, emulsion, spray, suspension, powder, foam, paste, granule, aerosol, or capsule in admixture with suitable carriers, diluents, adjuvants, preservatives, dispersants, solvents, and emulsifying agents suitable for physically or chemically associating with plants or their locus, and for oral uptake by pathogens.

21. The composition as claimed in claim 20, containing said fusion protein in an amount of between 0.1 and 99% by weight.

22. The composition as claimed in claim 20, containing said fusion protein in an amount of between 0.5% and 98% by weight.

23. The composition as claimed in claim 20, containing said fusion protein in an amount of between 1.0% and 95% by weight.

24. A process for the preparation of a composition as claimed in claim 20, further comprising the admixture of an amount of a fusion protein and any one or more of the following: carriers, diluents, adjuvants, preservatives, dispersants, solvents, or emulsifying agents, in effective pesticidal amount for the oral administration of an effective pesticidal amount of the fusion protein.

* * * * *